United States Patent [19]
Makovec et al.

[11] Patent Number: 5,962,502
[45] Date of Patent: Oct. 5, 1999

[54] POLYAMIDIC ACID DERIVATIVES WITH ANTIGASTRIN ACTIVITY, A METHOD FOR THEIR PREPARATION, AND THEIR PHARMACEUTICAL USE

[75] Inventors: Francesco Makovec, Monza; Walter Peris, Milan; Lucio C. Rovati; Luigi A. Rovati, both of Monza, all of Italy

[73] Assignee: Rotta Research Laboratorium S.p.A., Milan, Italy

[21] Appl. No.: 08/605,162

[22] PCT Filed: Sep. 7, 1994

[86] PCT No.: PCT/EP94/02983

§ 371 Date: Apr. 8, 1996

§ 102(e) Date: Apr. 8, 1996

[87] PCT Pub. No.: WO95/07261

PCT Pub. Date: Mar. 16, 1995

[30] Foreign Application Priority Data

Sep. 9, 1993 [IT] Italy ................... T093A0661

[51] Int. Cl.[6] ............... C07D 221/20; C07D 401/06; C07D 209/10; A61K 31/435

[52] U.S. Cl. .................. 514/415; 548/146; 548/214; 548/452; 548/469; 546/17; 546/268.1; 540/467; 540/480; 540/200; 540/484; 530/333; 530/337; 530/342

[58] Field of Search .................... 530/333, 337, 530/342; 548/452, 469, 473, 146, 214; 514/415; 546/17, 268.1; 540/467, 480, 484, 200

[56] References Cited

FOREIGN PATENT DOCUMENTS

WO 92/10479  6/1992  European Pat. Off. ...... C07D 221/20
WO 93/21172  10/1993  European Pat. Off. ...... C07D 295/08

OTHER PUBLICATIONS

Internationakl Search Report PCT/EP (94/02983) Jan. 16, 1995.
J. Med. Chem. 1992, 35, 28–38.
Chemical & Pharmacuetical Bulletin, vol. 36, No. 10, 1988 pp. 3961–3966.
Chemical & Pharmaceutical Bulletin, vol. 36, No. 9, 1988 pp. 3433–3438.

*Primary Examiner*—S. Mark Clardy
*Assistant Examiner*—Sabiha N. Qazl
*Attorney, Agent, or Firm*—Sughrue, Mion, Zinn, Macpeak & Seas, PLLC

[57] ABSTRACT

Derivatives of glutamic and aspartic of formula (I) are described

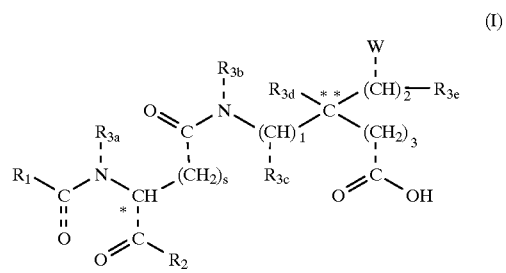

where the compounds are potent receptor antagonists of gastrin at the peripheral level and of cholecystokinin at the level of the central nervous system.

15 Claims, No Drawings

POLYAMIDIC ACID DERIVATIVES WITH ANTIGASTRIN ACTIVITY, A METHOD FOR THEIR PREPARATION, AND THEIR PHARMACEUTICAL USE

This application is a has been filed under 35 USC 371 or a national stage application of PCT/EP94/02983 filed Sep. 7, 1994.

The subject of the present invention is new derivatives of glutamic acid and of aspartic acid which can be represented by the general formula (I) indicated below:

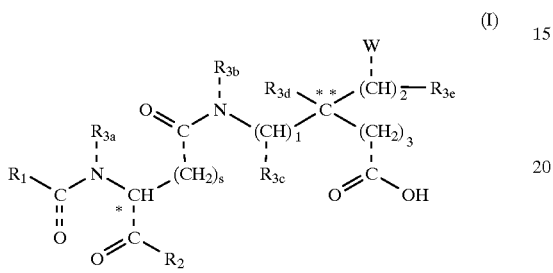

and in which s is 1 or 2, $R_1$ is selected independently from:

an unsubstituted or mono- or di-substituted phenyl group in which the substituents are selected from chloro, fluoro, bromo, trifluoromethyl, linear or branched $C_1$–$C_4$ alkyl, nitro, cyano, and methoxy groups, the 2-naphthyl group, the 2- (or 3-) indolyl group, and the 2- (or 3-) quinolinyl group, $R_2$ is selected independently from:

1) a heterocyclic spiro group represented by:

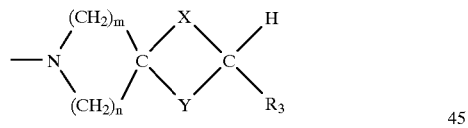

in which m and n are selected independently and may assume values of between 1 and 3 provided that the ring formed consists of at least 5 atoms, X and Y are selected independently from (CH—$R_3$)z, TCH$_2$ and CH$_2$T, where T is 0 (oxygen), or S and in which $R_3$ is a group selected independently from H, CH$_3$, and C$_2$H$_5$ and z may assume values of from 0 to 3, provided that the ring formed consists of at least 3 atoms;

2) an aminoalkyl adamantyl group represented by:

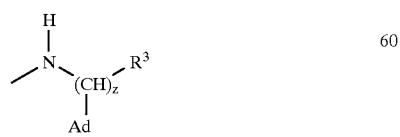

where z and $R_3$ have the meanings given above whilst Ad is adamantyl (1- or 2-yl).

3) an alkylamino group represented by:

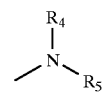

in which $R_4$ is a linear or branched alkyl chain containing from 4 to 10 carbon atoms, or a $C_5$–$C_{10}$ cycloalkyl group, or a linear or branched alkoxyalkyl group containing from 4 to 7 carbon atoms, and $R_5$ is selected independently from H, an alkyl group, a linear or branched alkoxyalkyl group containing from 1 to 7 carbon atoms, or a $C_5$–$C_{10}$ cycloalkyl group;

4) a $C_4$–$C_{10}$ cycloalkylamine;

5) a (condensed) dicyclic amino group represented by:

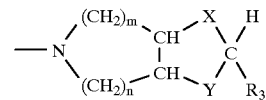

in which m, n, X, Y and $R_3$ have the meanings given above, $R_{3a}$, $R_{3b}$, and $R_{3d}$ are H or CH$_3$, $R_{3c}$, and $R_{3e}$ are 0 (zero), H or CH$_3$, $r_1$, raw and $r_3$ may independently assume whole values of between 0 and 2, W is selected independently from hydrogen, a linear or branched alkyl group containing from 1 to 6 carbon atoms, OH, OCH$_3$, SH, the benzyloxyl group, the thiomethyl group (CH$_3$—S—), or a group selected independently from a cycloalkane group, a heterocyclic group, a mono- or dicyclic aromatic or hydro-aromatic group having up to 10 carbon atoms, unsubstituted or substituted with substituents selected from fluoro, chloro, methyl, ethyl, trifluoromethyl, methoxy, cyano and nitro groups;

W may also be a CO—$R_6$ group where $R_6$ is selected independently from:

1) a linear or branched amino group represented by:

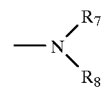

in which $R_7$ is selected from H and a linear or branched $C_1$–$C_5$ alkyl or alkoxyalkyl group and $R_8$ is selected from H, a $C_1$–$C_5$ alkyl group and a (CH$_2$)$_z$-Ar group, where z has the meaning given above and Ar is a phenyl group unsubstituted or mono- or di-substituted with substituents selected from fluoro, chloro, methyl, ethyl, trifluoromethyl and methoxy groups or the 1 (or 2)-naphthyl group;

2) a monocyclic aminoalkyl group represented by:

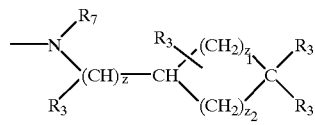

in which z, $R_3$ and $R_7$ are selected independently and have the meanings given above, $z_1$ and $z_2$ are selected independently and may assume values of between 1 and 4, provided that the ring formed includes between 4 and 10 carbon atoms;

3) a dicyclic aminospiro group represented by:

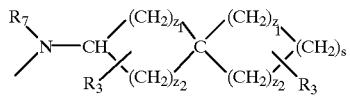

in which $R_3$, $R_7$, s, $z_1$ and $z_2$ have the meanings given above;

4) a dicyclic (orthofused) amino group, represented by:

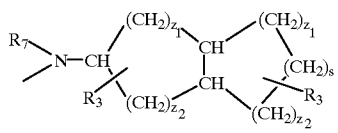

in which $R_3$, $R_7$, S, $z_1$ and $z_2$ have the meanings given above;

5) a dicyclic amino group represented by:

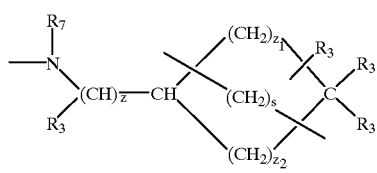

in which $R_3$, $R_7$, S, z, $z_1$ and $z_2$ have the meanings given above;

6) an azacycloalkyl group represented by:

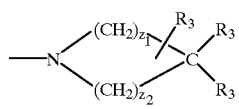

in which $R_3$, $z_1$ and $z_2$ have the meanings given above;

7) an azadicyclic (orthofused) group, represented by:

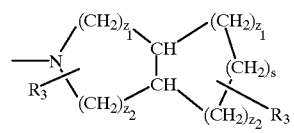

in which $R_3$, s, $z_1$ and $z_2$ have the meanings given above;

8) a dicyclic azaspiro group represented by:

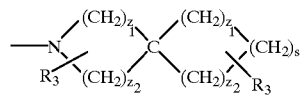

in which $R_3$, s, $z_1$ and $z_2$ have the meanings given above;

9) an azadicyclic group represented by:

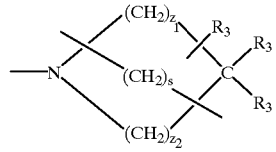

in which $R_3$, s, $z_1$ and $z_2$ have the meanings given above;

10) an azacycloalkyl group represented by:

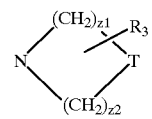

in which $R_3$, $z_1$, $z_2$ and T have the meanings given above;

11) an aminoalkyl adamantyl group represented by:

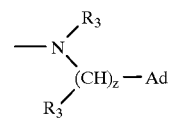

in which $R_3$ and z have the meanings given above and Ad is adamantyl (1- or 2-yl).

Some of the compounds according to the invention may be represented better by the general formula (II) indicated below:

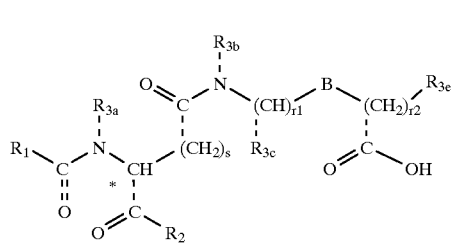

(II)

in which:

$R_1$, $R_2$, $R_{3a}$, $R_{3b}$, $R_{3c}$, $R_{3e}$, s, $r_1$ and $r_2$ have the meanings given above, and B is selected independently from a cycloalkane group, a heterocyclic group, a mono- or dicyclic aromatic or hydro-aromatic group having up to 10 carbon atoms, unsubstituted or mono- or di-substituted with substituents selected independently from hydrogen, fluoro, chloro, trifluoromethyl, methyl, ethyl, methoxy, cyano and nitro groups.

Finally, some of the compounds according to the invention may be represented by the general formula (III) indicated below:

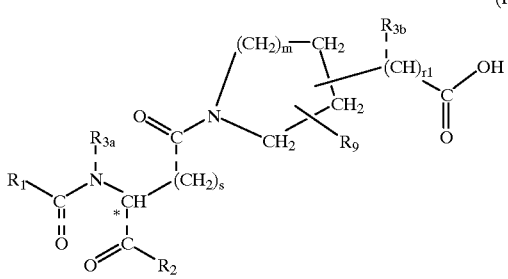

(III)

in which $R_1$, $R_2$, $R_{3a}$, $R_{3b}$, s, m and $r_1$ have the meanings given above and $R_9$ is selected independently from hydrogen, a linear or branched $C_1$–$C_5$ alkyl group, the phenyl group and the benzyl group.

The stereochemistry of the chiral centre marked * in FIGS. I, II and III is in the R (Rectus=D) configuration. The stereochemistry of the carbon atom marked ** in FIG. I, which may become asymmetrical, according to the substituents bonded thereto, may be R (Rectus), racemic [R (Rectus), S(Sinister)], or S (Sinister).

Preferably, s is 2, $R_1$ is a phenyl group substituted with the chloro group in positions 3 and 5, $R_2$ is preferably the 8-azaspiro[4.5]decan-8-yl group, $r_1$ and $r_3$ are 0 (zero) or 1, $r_2$ is 1, W is preferably selected from the phenyl, 3-indolyl and 1-naphthyl groups, and the stereochemistry of the chiral centre marked ** in the general formula (I) is R (Rectus).

The compounds of the present invention have been found to be potent receptor antagonists of gastrin at the peripheral level, that is, at the level of the gastro-intestinal system, and potent receptor antagonists of cholecystokinin (CCK) at the level of the central nervous system (CCK-B-antagonists). It can therefore be considered that they may be used to advantage in the treatment of various diseases in man linked to imbalances in the physiological levels of gastrin and of CCK or of other biologically active polypeptides related thereto, both at the level of the gastro-intestinal system and at the level of the central nervous system (CNS) or in other organs and systems in which these biologically active peptides play a physiological or pathological role. Thus, for example, it is possible to predict the advantageous use of these compounds, at the gastro-intestinal level, for the treatment of diseases linked to disturbances of motility and mucotrophism such as, for example, gastritis, peptic ulcers, colitis or certain gastro-intestinal tumors which are sustained by gastrin or polypeptide hormones related thereto and, at the level of the CNS, for the treatment of mental disorders such as, for example, anxiety, panic attacks, and psychoses such as, for example, schizophrenia, anorexia, etc. Another use could be the treatment and prevention of some eye pathological conditions such as, for example, myosis induced by the surgical treatment of cataracts or chronic eye inflammations.

Pharmaceutical forms of the compounds of the invention such as, for example, pills, capsules, suspensions, solutions and suppositories, can be prepared according to conventional techniques and may be administered by oral, parenteral, rectal or ocular routes or other administration forms suitable to obtain the therapeutical effect.

The active ingredient is typically administered to the patient in a ratio of from 0.01 to 10 mg/kg of body weight per dose. For parenteral and ocular administration, the use of a water-soluble salt of a compound of the invention, such as the sodium salt or another non-toxic and pharmaceutically-acceptable salt is preferable. Substances commonly used in pharmaceutical techniques such as excipients, binders, flavorings, dispersants, colorants, humectants, etc. may be used as inactive ingredients.

The method for the preparation of the derivatives of glutamic acid and aspartic acid according to the invention consists of the amidation of acid derivatives of formula

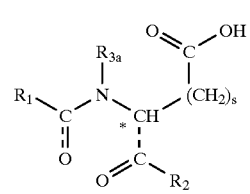

(IV)

in which s, $R_1$, $R_2$ and $R_{3a}$ have the meanings given above, with suitable amino-acids of formula (V):

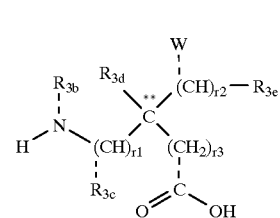

(V)

in which $R_{3b}$, $R_{3c}$, $R_{3d}$, $R_{3e}$, $r_1$, $r_2$, $r_3$ and W have the meanings given above, or with suitable amino-acids of formula (VI):

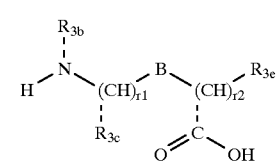

(VI)

in which $R_{3b}$, $R_{3c}$, $R_{3e}$, $r_1$, $r_2$ and B have the meanings indicated above, or with suitable amino-acids of formula (VII):

(VII)

where m, $r_1$, $R_3$ and $R_9$ have the meanings indicated above, to give the corresponding derivatives of formulae (I), (II) and (III), respectively, according to the following general scheme:

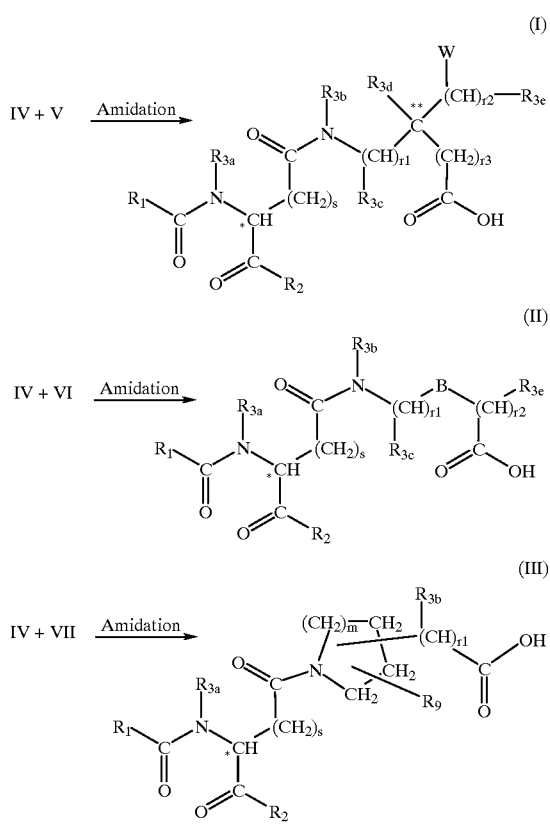

The amidation process is preferably carried out with the use of the mixed anhydride method in an inert solvent at a temperature between −15° and +15° or by other suitable conventional methods.

The initial acid intermediates of formula (IV) were prepared as described by [Makovec et al, J. Med. Chem. 35 (1992), 28–38], and the amino-acids of formula (V), (VI) and (VII) are available commercially or were prepared by conventional methods described in the literature. The following examples are given to illustrate the invention further.

EXAMPLE 1

Preparation of: (R,R)-1[(1-carboxy-2-phenylethyl) amino]-1 oxo-5-(8-azaspiro[4.5]decan-8-yl)-4-(3,5-dichloro-benzoylamino)-5-oxopentanoic acid.

[Compound 9 (General formula I)—Table I].

60 g (0.136 moles) of (R)-5-(8-azaspiro[4.5]decan-8-yl)-4-(3,5-dichloro-benzoylamino)-5-oxopentanoic acid (CR 2194) and 20 ml of triethylamine (0.1435 moles) were dissolved at room temperature in 1000 ml of tetrahydrofuran (THF) and the mixture was cooled to −10° C. This temperature was maintained and 14 ml of ethyl chloroformate (0.1469 moles) were added. Upon completion of the addition, the mixture was left to react for 15 minutes, still at low temperature, and then 26 g of D-phenylalanine (0.164 moles) dissolved in 1000 ml of an $H_2O$/THF mixture were added slowly, the temperature being kept below −5° C. Upon completion of the addition, the reaction mass was kept at low temperature for a further hour and then at room temperature for about 12 hours. The solvent was evaporated under vacuum. The residue was taken up with ethyl acetate and washed with HCl and $H_2O$ to eliminate the unreacted amino-acid. After drying, the solvent was evaporated and the oily residue was precipitated with petroleum ether.

The crude product was crystallized by acetonitrile. After cooling, the precipitate was filtered and dried at 60° C. in an oven under air circulation, producing 66 g (0.112 moles) of the product with a yield of 82% ($C_{30}H_{35}Cl_2N_3O_5$).

M.P. 106–108° C.

TLC (isoamyl alcohol-acetone-$H_2O$ 5:2:1)—Rf 0.47 Specific rotation $[\alpha_D]=-51.3°$ (2% in $CHCl_3$).

EXAMPLE 2

Preparation of (R)-1-[N-methyl-(4-carboxy-phenyl) amino]1-oxo-5-(8-azaspiro[4.5]decan-8-yl)-4-(3,5-dichloro-benzoylamino]-5-oxopentanoic acid.

[Compound 51 (General formula II)—Table II].

The method described in Example 1 was used, first of all by reacting 60 g (0.136 moles) of (R)-5-(8-azaspiro[4.5] decan-8-yl)-4-(3,5-dichloro-benzoylamino)-5-oxopentanoic acid (CR 2194) with 14 ml of ethyl chloroformate (0.1469 moles) in the presence of 20 ml of triethylamine (0.1435 moles) in THF and then by reacting the mixed anhydride thus formed with 25.5 g (0.1685 moles) of N-methyl-anthranylic acid dissolved in THF. Upon completion of the reaction, the reaction mixture was treated as described in Example 1. The crude oily residue was solidified by standing with isopropyl ether. The crude product was crystallized by acetonitrile. After cooling, the precipitate was filtered and dried at 60° C. in an oven under air circulation, producing 53.1 g (0.092 moles) of the product with a yield of 68% ($C_{29}H_{33}Cl_2N_3O_5$).

M.P. 134–135° C.; TLC (isoamyl alcohol-acetone-$H_2O$ 5:2:1)—Rf 0.52. Specific rotation $[\alpha_D]=-44.2°$ (2% in $CHCl_3$).

EXAMPLE 3

Preparation of (R)-1-(piperidine-3-carboxy)-1-oxo-5-(8-azaspiro[4.5]decan-8-yl)-4-(3,5-dichloro-benzoylamino)-5-oxopentanoic acid.

[Compound 58 (general formula III)]

The method described in Example 1 was again used in this case, first of all by reacting 60 g (0.136 moles) of (R)-5-(8-azaspiro[4.5]decan-8-yl)-4-(3,5-dichloro-benzoylamino)-5-oxopentanoic acid (CR 2194) with 14 ml of ethyl chloroformate (0.1469 moles) in the presence of 20 ml of triethylamine (0.1435 moles) in THF and then by reacting the mixed anhydride thus formed with 19.2 g (0.1685 moles) of piperidine-3-carboxylic acid dissolved in THF/$H_2O$. Upon completion of the reaction the reaction mixture was treated as described in Example 1. The crude oily residue thus obtained was precipitated by treatment with ligroin. The crude product was crystallized by acetonitrile. After cooling, the precipitate was filtered and dried at 60° C. under vacuum, producing 47.3 g (0.086 moles) of the pure product with a yield of 63% ($C_{27}H_{35}Cl_2N_3O_5$).

M.P. 114–117° C. TLC (isoamyl alcohol-acetone-$H_2O$ 5:2:1)—Rf 0.74. Specific rotation $[\alpha_D]=-47.0°$ (0.5% in $CHCl_3$).

All the compounds of formulae I, II and III (see Scheme 1) were synthesized with the use of the same method. Tables I and II below give some derivatives of formula I and of formula II thus obtained with some chemical and physical identifying characteristics.

TABLE 1

COMPOUNDS OF GENERAL FORMULA (1)

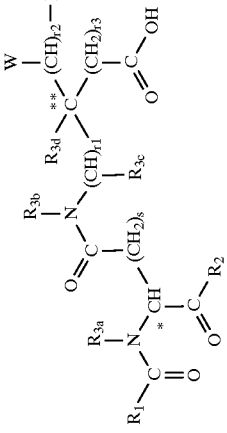

| COMPOUND | R₁ | R₂ | s | R₃ a | R₃ b | R₃ c | R₃ d | R₃ e | r₁ | r₂ | r₃ | W | FORMULA | MELTING POINT (C.)° | TLC (Rf) Note 1 | SPECIFIC ROTATION (Note 2) (Note 3) Configuration |
|---|---|---|---|---|---|---|---|---|---|---|---|---|---|---|---|---|
| 1 | 3,5-dichlorophenyl | 8-azaspiro[4.5]decan-8-yl | 2 | H | H | / | H | / | 0 | 0 | 0 | H | $C_{23}H_{29}Cl_2N_3O_5$ | 86/88 | 0.34 | −39.1 / |
| 2 | 3,5-dichlorophenyl | 8-azaspiro[4.5]decan-8-yl | 2 | H | $CH_3$ | / | H | / | 0 | 0 | 0 | H | $C_{24}H_{31}Cl_2N_3O_5$ | 103/105 | 0.23 | −39.6 / |
| 3 | 3,5-dichlorophenyl | 8-azaspiro[4.5]decan-8-yl | 2 | H | H | H | H | / | 1 | 0 | 0 | H | $C_{24}H_{31}Cl_2N_3O_5$ | 71/74 | 0.57 | −40.0 / |
| 4 | 3,5-dichlorophenyl | 8-azaspiro[4.5]decan-8-yl | 2 | H | H | H | H | / | 2 | 0 | 0 | H | $C_{25}H_{33}Cl_2N_3O_5$ | 94/96 | 0.51 | −42.3 / |
| 5 | 3,5-dichlorophenyl | 8-azaspiro[4.5]decan-8-yl | 2 | H | H | / | H | H | 0 | 1 | 0 | H | $C_{24}H_{31}Cl_2N_3O_5$ | 108/111 | 0.36 | −36.6 R,S |
| 6 | 3,5-dichlorophenyl | 8-azaspiro[4.5]decan-8-yl | 2 | H | H | / | H | H | 0 | 1 | 0 | Isopropyl | $C_{27}H_{37}Cl_2N_3O_5$ | 84/86 | 0.72 | −31.2 R,S |
| 7 | 3,5-dichlorophenyl | 8-azaspiro[4.5]decan-8-yl | 2 | H | H | / | H | H | 0 | 2 | 0 | $SCH_3$ | $C_{26}H_{33}Cl_2N_3O_5S$ | 101/104 | 0.57 | −11.1 R,S |
| 8 | 3,5-dichlorophenyl | 8-azaspiro[4.5]decan-8-yl | 2 | H | H | / | H | H | 0 | 1 | 0 | Phenyl | $C_{30}H_{35}Cl_2N_3O_5$ | 108/110 | 0.51 | −47.3 R,S |
| 9 | 3,5-dichlorophenyl | 8-azaspiro[4.5]decan-8-yl | 2 | H | H | / | H | H | 0 | 1 | 0 | Phenyl | $C_{36}H_{35}Cl_2N_3O_5$ | 106/109 | 0.47 | −51.3 R |
| 10 | 3,5-dichlorophenyl | 8-azaspiro[4.5]decan-8-yl | 2 | H | H | / | H | H | 0 | 1 | 0 | Phenyl | $C_{30}H_{35}Cl_2N_3O_5$ | 116/118 | 0.48 | −36.6 S |
| 11 | 3,5-dichlorophenyl | 8-azaspiro[4.5]decan-8-yl | 2 | H | $CH_3$ | / | H | H | 0 | 1 | 0 | Phenyl | $C_{31}H_{37}Cl_2N_3O_5$ | 107/109 | 0.40 | −23.2 R,S |
| 12 | 3,5-dichlorophenyl | 8-azaspiro[4.5]decan-8-yl | 2 | H | $CH_3$ | / | H | H | 0 | 1 | 0 | Phenyl | $C_{31}H_{37}Cl_2N_3O_5$ | 118/120 | 0.38 | +1.8 R |
| 13 | 3,5-dichlorophenyl | 8-azaspiro[4.5]decan-8-yl | 2 | H | H | / | H | / | 0 | 0 | 0 | Phenyl | $C_{29}H_{31}Cl_2N_3O_5$ | 105/107 | 0.44 | −27.2 R |
| 14 | 3,5-dichlorophenyl | 8-azaspiro[4.5]decan-8-yl | 2 | H | H | / | H | H | 0 | 0 | 1 | Phenyl | $C_{32}H_{37}Cl_2N_3O_5$ | 94/96 | 0.77 | −37.3 S |
| 15 | 3,5-dichlorophenyl | 8-azaspiro[4.5]decan-8-yl | 2 | H | H | / | H | H | 0 | 1 | 1 | Phenyl | $C_{31}H_{37}Cl_2N_3O_5$ | 85/87 | 0.51 | −51.4 R |
| 16 | 3,5-dichlorophenyl | 8-azaspiro[4.5]decan-8-yl | 2 | H | H | / | H | H | 0 | 2 | 0 | Phenyl | $C_{31}H_{37}Cl_2N_3O_5$ | 101/104 | 0.56 | −21.6 R,S |

TABLE 1-continued

COMPOUNDS OF GENERAL FORMULA (1)

$$\begin{array}{c} R_{3b} \\ R_1-C(=O)-N(R_{3a})-CH^*-C(=O)-R_2 \\ (CH_2)_s-C(=O)-N(R_{3b})-(CH_2)_{r1}-C(R_{3c})(r_2)-**C(R_{3d})((CH_2)_{r2}-R_{3e})-(CH_2)_{r3}-COOH \\ \text{with side chain terminating in W} \end{array}$$

| COMPOUND | R$_1$ | R$_2$ | s | R$_3$ a | b | c | d | e | r$_1$ | r$_2$ | r$_3$ | W | FORMULA | MELTING POINT (°C) | TLC (Rf) Note 1 | SPECIFIC ROTATION (Note 2) Configuration (Note 3) |
|---|---|---|---|---|---|---|---|---|---|---|---|---|---|---|---|---|
| 17 | 3,5-dichlorophenyl | 8-azaspiro[4.5]decan-8-yl | 2 | H | H | / | H | H | 0 | 0 | 0 | 4-chlorophenyl | C$_{30}$H$_{34}$Cl$_2$N$_3$O$_5$ | 117/119 | 0.46 | −37.0 R,S |
| 18 | 3,5-dichlorophenyl | 8-azaspiro[4.5]decan-8-yl | 2 | H | H | / | H | H | 0 | 1 | 0 | 4-hydroxyphenyl | C$_{30}$H$_{35}$Cl$_2$N$_3$O$_6$ | 147/150 | 0.62 | −32.3 R,S |
| 19 | 3,5-dichlorophenyl | 8-azaspiro[4.5]decan-8-yl | 2 | H | H | / | H | H | 0 | 0 | 0 | 3-indolyl | C$_{32}$H$_{35}$Cl$_2$N$_4$O$_5$ | 103/105 | 0.67 | −38.4 R,S |
| 20 | 3,5-dichlorophenyl | 8-azaspiro[4.5]decan-8-yl | 2 | H | H | / | H | H | 0 | 1 | 0 | 3-indolyl | C$_{32}$H$_{36}$Cl$_2$N$_5$O$_5$ | 103/105 | 0.66 | −45.1 S |
| 21 | 3,5-dichlorophenyl | 8-azaspiro[4.5]decan-8-yl | 2 | H | H | / | H | H | 0 | 1 | 0 | 3-indolyl | C$_{32}$H$_{36}$Cl$_2$N$_5$O$_5$ | 137/138 | 0.67 | −29.4 R |
| 22 | 3,5-dichlorophenyl | 8-azaspiro[4.5]decan-8-yl | 2 | H | CH$_3$ | / | H | H | 0 | 1 | 0 | 3-indolyl | C$_{33}$H$_{35}$Cl$_2$N$_4$O$_5$ | 112/113 | 0.51 | −45.8 S |
| 23 | 3,5-dichlorophenyl | 8-azaspiro[4.5]decan-8-yl | 2 | H | H | / | H | H | 0 | 1 | 0 | Benzyloxy | C$_{31}$H$_{37}$Cl$_2$N$_3$O$_6$ | 92/94 | 0.48 | −35.8 R |
| 24 | 3,5-dichlorophenyl | 8-azaspiro[4.5]decan-8-yl | 2 | H | H | / | H | H | 0 | 1 | 0 | 2-naphthyl | C$_{34}$H$_{37}$Cl$_2$N$_3$O$_5$ | 108/110 | 0.44 | −55.5 R |
| 25 | 3,5-dichlorophenyl | 8-azaspiro[4.5]decan-8-yl | 2 | H | H | / | H | H | 0 | 1 | 0 | 1-naphthyl | C$_{34}$H$_{37}$Cl$_2$N$_3$O$_5$ | 106/108 | 0.50 | −3.4 R |
| 26 | 3,5-dichlorophenyl | 8-azaspiro[4.5]decan-8-yl | 2 | H | H | / | H | H | 0 | 1 | 0 | 3-pyridyl | C$_{29}$H$_{34}$Cl$_2$N$_4$O$_5$ | 105/106 | 0.31 | −81.8 R |
| 27 | 3,5-dichlorophenyl | 8-azaspiro[4.5]decan-8-yl | 2 | H | H | / | H | H | 0 | 1 | 0 | 2-pyridyl | C$_{29}$H$_{34}$Cl$_2$N$_4$O$_5$ | 101/103 | 0.29 | −73.1 R |
| 28 | 3,5-dichlorophenyl | 8-azaspiro[4.5]decan-8-yl | 2 | H | H | / | H | H | 0 | 1 | 0 | Cyclohexyl | C$_{30}$H$_{41}$Cl$_2$N$_3$O$_5$ | 154/156 | 0.66 | −23.9 R |
| 29 | 2-naphthyl | 8-azaspiro[4.5]decan-8-yl | 2 | H | H | / | H | H | 0 | 1 | 0 | 3-indolyldecan-8-yl | C$_{35}$H$_{40}$N$_4$O$_5$ | 115/117 | 0.63 | −42.5 R |
| 30 | 3,5-dichlorophenyl | 3-azaspiro[5.5]undecan-3-yl | 2 | H | H | / | H | H | 0 | 1 | 0 | 3-indolyl | C$_{33}$H$_{38}$Cl$_2$N$_4$O$_5$ | 146/148 | 0.43 | −32.2 R |
| 31 | 3-chlorophenyl | [2-(1-adamantyl)ethylamino] | 2 | H | H | / | H | H | 0 | 1 | 0 | 3-indolyl | C$_{35}$H$_{41}$ClN$_4$O$_5$ | 142/145 | 0.40 | −2.7 R |
| 32 | 3-methylphenyl | 8-azaspiro[4.5]decan-8-yl | 2 | H | H | / | H | H | 0 | 1 | 0 | 3-indolyl | C$_{33}$H$_{40}$N$_4$O$_5$ | 127/130 | 0.53 | −38.5 R |
| 33 | 3-chlorophenyl | (3,3-dimethylbutyl)amino | 2 | H | H | / | H | H | 0 | 1 | 0 | Phenyl | C$_{27}$H$_{34}$ClN$_3$O$_5$ | 180/182 | 0.46 | −5.9* |

TABLE 1-continued

COMPOUNDS OF GENERAL FORMULA (1)

$$\begin{array}{c} R_{3a} \\ R_1-C(=O)-N-CH^*(C(=O)-R_2)-(CH_2)_s-C(=O)-N(R_{3b})-R_3 \end{array}$$

$R_3 = -(CH_2)_{r1}-C^{**}(R_{3c})(R_{3d})-(CH_2)_{r2}-R_{3e}$ with $-(CH_2)_{r3}-COOH$ and W

| COMPOUND | R$_1$ | R$_2$ | s | a | b | c | d | e | r$_1$ | r$_2$ | r$_3$ | W | FORMULA | MELTING POINT (C.)° | TLC (Rf) Note 1 | SPECIFIC ROTATION (Note 2) Configuration (Note 3) |
|---|---|---|---|---|---|---|---|---|---|---|---|---|---|---|---|---|
| 34 | 3,5-dichlorophenyl | 8-azaspiro[4.5]decan-8-yl | 2 | H | H | / | H | / | 0 | 0 | 2 | (4,4-dimethylcyclohexyl)aminocarbonyl | C$_{34}$H$_{48}$Cl$_2$N$_4$O$_6$ | 228/230 | 0.46 | R,S −43.9 |
| 35 | 3,5-dichlorophenyl | 8-azaspiro[4.5]decan-8-yl | 2 | H | H | / | H | / | 0 | 0 | 2 | (4,4-dimethylcyclohexyl)aminocarbonyl | C$_{34}$H$_{45}$Cl$_2$N$_4$O$_6$ | 182/184 | 0.66 | S −15.2 |
| 36 | 3,5-dichlorophenyl | 8-azaspiro[4.5]decan-8-yl | 2 | H | H | / | H | / | 0 | 0 | 2 | 8-azaspiro[4.5]decan-8-yl-carbonyl | C$_{35}$H$_{48}$Cl$_2$N$_4$O$_6$ | 132/134 | 0.71 | R −27.9 |
| 37 | 3,5-dichlorophenyl | 8-azaspiro[4.5]decan-8-yl | 2 | H | H | / | H | / | 0 | 0 | 2 | N-methylphenylaminocarbonyl | C$_{33}$H$_{40}$Cl$_2$N$_4$O$_6$ | 109/111 | 0.53 | R −57.6 |
| 38 | 3,5-dichlorophenyl | 8-azaspiro[4.5]decan-8-yl | 2 | H | H | / | H | / | 0 | 0 | 2 | N-methylbenzylaminocarbonyl | C$_{34}$H$_{42}$Cl$_2$N$_4$O$_6$ | 119/121 | 0.57 | R −11.6 |
| 39 | 3,5-dichlorophenyl | 8-azaspiro[4.5]decan-8-yl | 2 | H | H | / | H | / | 0 | 0 | 2 | 2naphthylaminocarbonyl | C$_{36}$H$_{40}$Cl$_2$N$_4$O$_6$ | 171/173 | 0.63 | +23.2* R |
| 40 | 3,5-dichlorophenyl | 8-azaspiro[4.5]decan-8-yl | 2 | H | H | / | H | / | 0 | 0 | 2 | [2-(1-adamantyl)ethyl]aminocarbonyl | C$_{38}$H$_{52}$Cl$_2$N$_4$O$_6$ | 141/143 | 0.72 | ±10.3 R |
| 41 | 3,5-dichlorophenyl | 8-azaspiro[4.5]decan-8-yl | 2 | H | H | / | H | / | 0 | 0 | 2 | Phenethylaminocarbonyl | C$_{34}$H$_{42}$Cl$_2$N$_4$O$_6$ | 127/128 | 0.54 | −13.5 R |
| 42 | 2-naphthyl | dipentylamino | 2 | H | H | / | H | H | 0 | 1 | 0 | 3-indolyl | C$_{37}$H$_{46}$N$_4$O$_5$ | 85/86 | 0.60 | −33.5 R |
| 43 | 3,5-dichlorophenyl | 8-azaspiro[4.5]decan-8-yl | 1 | H | H | / | H | H | 0 | 1 | 0 | 3-indolyl | C$_{31}$H$_{34}$Cl$_2$N$_4$O$_5$ | 240/242 | 0.40 | −13.1* R |
| 44 | 3,5-dichlorophenyl | 8-azaspiro[4.5]decan-8-yl | 1 | H | H | / | H | H | 0 | 1 | 0 | Phenyl | C$_{29}$H$_{33}$Cl$_2$N$_3$O$_5$ | 222/223 | 0.39 | −20.1* R |
| 45 | 3,5-dichlorophenyl | 8-azaspiro[4.5]decan-8-yl | 2 | H | H | / | CH$_3$ | H | 0 | 1 | 0 | Phenyl | C$_{31}$H$_{37}$Cl$_2$N$_3$O$_5$ | 117/120 | 0.50 | −33.9* R,S |
| 46 | 3,5-dichlorophenyl | 8-azaspiro[4.5]decan-8-yl | 2 | CH$_3$ | H | / | H | H | 0 | 1 | 0 | 3-indolyl | C$_{33}$H$_{35}$Cl$_2$N$_4$O$_5$ | 102/105 | 0.57 | −44.6 R |

TABLE 2

COMPOUNDS OF GENERAL FORMULA (II)

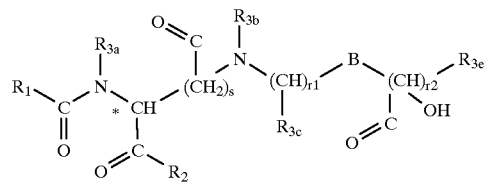

| COM-POUND | $R_1$ | $R_2$ | s | a | b | c | e | $r_1$ | $r_2$ | B | FORMULA | MELTING POINT (C.)° | TLC (Rf) Note 1 | SPECIFIC ROTATION (Note 2) |
|---|---|---|---|---|---|---|---|---|---|---|---|---|---|---|
| 47 | 3,5-dichlorophenyl | 8-azaspiro[4.5]decan-8-yl | 2 | H | H | / | / | 0 | 0 | p-Phenylene | $C_{28}H_{31}Cl_2N_3O_5$ | 281/282 | 0.79 | 39.7* |
| 48 | 3,5-dichlorophenyl | 8-azaspiro[4.5]decan-8-yl | 2 | H | $CH_3$ | / | / | 0 | 0 | p-Phenylene | $C_{29}H_{33}Cl_2N_3O_5$ | 108/110 | 0.65 | −6.2** |
| 49 | 3,5-dichlorophenyl | 8-azaspiro[4.5]decan-8-yl | 2 | H | H | / | / | 0 | 0 | m-Phenylene | $C_{28}H_{31}Cl_2N_3O_5$ | 261/263 | 0.87 | 32.4* |
| 50 | 3,5-dichlorophenyl | 8-azaspiro[4.5]decan-8-yl | 2 | H | H | / | / | 0 | 0 | o-Phenylene | $C_{28}H_{31}Cl_2N_3O_5$ | 215/217 | 0.72 | 74.3** |
| 51 | 3,5-dichlorophenyl | 8-azaspiro[4.5]decan-8-yl | 2 | H | $CH_3$ | / | / | 0 | 0 | o-Phenylene | $C_{29}H_{33}Cl_2N_3O_5$ | 134/135 | 0.52 | −44.2** |
| 52 | 3,5-dichlorophenyl | 8-azaspiro[4.5]decan-8-yl | 2 | H | H | / | / | 0 | 0 | 2-methyl-p phenylene (i.e. 4-carboxy) | $CH_{29}H_{33}Cl_2N_3O_5$ | 269/271 | 0.76 | 36.4* |
| 53 | 3,5-dichlorophenyl | (3,3-dimethyl butyl)amino | 2 | H | H | / | / | 0 | 0 | p-Phenylene | $C_{25}H_{29}Cl_2N_3O_5$ | 241/243 | 0.89 | 14.6** |
| 54 | Phenyl | 8-azaspiro[4.5]decan-8-yl | 2 | H | H | / | / | 0 | 0 | p-Phenylene | $C_{28}H_{33}N_3O_5$ | 146/149 | 0.71 | −17.5** |
| 55 | 3,5-dichlorophenyl | 8-azaspiro[4.5]decan-8-yl | 1 | H | H | / | / | 0 | 0 | o-Phenylene | $C_{27}H_{29}Cl_2N_3O_5$ | 128/130 | 0.58 | 12.1** |
| 56 | 3,5-dichlorophenyl | 8-azaspiro[4.5]decan-8-yl | 2 | H | H | H | / | 1 | 0 | p-Phenylene | $C_{29}H_{33}Cl_2N_3O_5$ | 118/120 | 0.79 | −7.5** |
| 57 | 3,5-dichlorophenyl | 8-azaspiro[4.5]decan-8-yl | 2 | H | H | / | H | 0 | 1 | p-Phenylene | $C_{29}H_{33}Cl_2N_3O_5$ | 116/169 | 0.63 | −12.4** |

Note 1: Eluent, isoamyl alcohol/acetone/$H_2O$ 5:2:1 (v/v)
Note 2: (*) $[\alpha]_D$ in pyridine; (**) $[\alpha]_D$ in chloroform Description of Pharmacological Activity
1) Anticholecystokinin (Anti CCK-B) Activity in vitro The ability of the compounds of the invention to interact with the central CCK-B receptor was evaluated with the use of non-sulphated [3-H] [N-methyl-N-leucine]CCK-8, which has been found to be a very selective ligand for the CCK-B receptors, having an affinity approximately 4000 times greater for the receptors of the cortex (CCK-B) than for those of the pancreas (CCK-A) in the guinea-pig [Knapp et al; J. Pharmacol. and Exp. Therap. 225 (3) (1990), 1278–1286].

Cerebral cortices of male white guinea-pigs were thus used, according to the method mentioned above, so as to obtain a membrane content corresponding to about 300 mcg of proteins/ml. The membranes were incubated together with the radioactive tracer and the compounds under test for 150 minutes at 25° C. After the supernatant had been discarded, the radioactivity associated with the pellet was determined with a liquid scintillator. The specific binding was determined as the difference between the binding in the absence and in the presence of $5.10^{-6}M$ CCK-8. The results obtained are shown in Table 3, in which the $IC_{50}$, that is, the concentration (in micromoles/liter) of the antagonist which could displace 50% of the [3-H] [N-methyl-N-leucine] CCK-8 from the receptor is given.

TABLE 3

Inhibition of the binding of (3-H) [N-methyl-N-leucine] CCK-8 to guinea-pig cortical membranes

| Compounds | $IC_{50}$ (micromoles /liter) | Compounds | $IC_{50}$ (micromoles /liter) | Compounds | $IC_{50}$ (micromoles /liter) |
|---|---|---|---|---|---|
| 1 | 1.06 | 21 | 0.04 | 41 | 0.79 |
| 2 | 0.61 | 22 | 0.38 | 42 | 1.88 |
| 3 | 0.73 | 23 | 0.27 | 43 | 1.03 |
| 4 | 1.25 | 24 | 0.13 | 44 | 0.35 |
| 5 | 1.32 | 25 | 0.07 | 45 | 0.58 |

TABLE 3-continued

Inhibition of the binding of (3-H) [N-methyl-N-leucine] CCK-8 to guinea-pig cortical membranes

| Compounds | $IC_{50}$ (micromoles /liter) | Compounds | $IC_{50}$ (micromoles /liter) | Compounds | $IC_{50}$ (micromoles /liter) |
|---|---|---|---|---|---|
| 6 | 0.38 | 26 | 0.25 | 46 | 0.12 |
| 7 | 0.51 | 27 | 0.15 | 47 | 1.72 |
| 8 | 0.20 | 28 | 0.65 | 48 | 0.44 |
| 9 | 0.15 | 29 | 13.3 | 49 | 1.39 |
| 10 | 0.73 | 30 | 0.10 | 50 | 0.45 |
| 11 | 0.22 | 31 | 13.9 | 51 | 0.12 |
| 12 | 0.10 | 32 | 3.56 | 52 | 2.77 |
| 13 | 0.42 | 33 | IN* | 53 | 6.40 |
| 14 | 0.34 | 34 | 0.73 | 54 | 9.21 |
| 15 | 0.22 | 35 | 1.70 | 55 | IN* |
| 16 | 0.30 | 36 | 1.70 | 56 | 19.5 |
| 17 | 0.68 | 37 | 0.70 | 57 | 7.73 |
| 18 | 0.32 | 38 | 0.18 | 58 | 0.64 |
| 19 | 0.05 | 39 | 0.70 | CR 2194 | 2.40 |
| 20 | 0.22 | 40 | IN* | Pentagastrin | 0.003 |
|   |      |    |     | S-9** | 38.6 |

Note (*): IN (inactive) when the $IC_{50}$ is >$3.10^{-5}$ M.
Note (**): S (Sinister) diastereoisomer of compound 9

It can be seen from the data given in Table 3 that many of the compounds of the invention such as, for example, compounds 12, 19, 21, 25 and 30, are potent inhibitors of the binding of [N-methyl-N-leucine]CCK-8 to the receptors of the cortical membranes of guinea-pigs. In fact, some of them are up to 50 times more potent than their precursor, that is, the gastrin antagonist CR 2194, whilst they are only 10–15 times less active than the specific antagonist, pentagastrin. The displacement activity is greatly affected by the stereochemistry at the level of the glutamic (or aspartic) component, respectively, which is indicated (*) in the compounds of formulae I, II and III.

In fact, compound S-9, which was synthesized for comparative purposes and is not a subject of the present invention, was about 250 times less active than its R diastereoisomer, compound 9. The stereochemistry connected with the carbon atom indicated (**) in the compounds of formula I has less effect on antigastrin activity and depends greatly on the nature of the groups bound thereto. In fact, for example, although compound 9 (R) and compound 21 (R) are about 5 times more active than their corresponding (S) diastereoisomers, that is, compounds 10 and 20, compound 15 (R) is only 1.5 times more active than its (S) diastereoisomer 14, whilst compound 34 (S) is actually about twice as active as its R diastereoisomer, compound 35.

2) Antigastrin Activity (peripheral) in Rabbit Gastric Mucous-Membrane Cells in vitro The parietal cells of the gastric mucous membrane are responsible for the secretion of HCl. They have specific membrane receptors which can be activated by gastrin and which have been defined as gastrin receptors or type-B cholecystokinin (CCK-B) receptors.

Since it has been observed that the activation of the CCK-B receptors by gastrin leads to an increase in the cytosolic levels of calcium ions, a technique involving the measurement of the increase in intracellular calcium induced by gastrin in the presence and in the absence of the compounds of the invention was used as an index of the antigastrin activity of the compounds. Rabbit gastric mucous-membrane cells were prepared by conventional techniques with the use of collagenase and pronase as digestive enzymes.

The cellular preparation obtained by the enzymatic digestion was composed of parietal cells, zymogen cells and mucous-membrane cells. The percentage of parietal cells present was not sufficient to be able to demonstrate a response to gastrin in the experimental model considered. For this reason, the preparation was enriched with parietal cells by elutration until a parietal-cells content of about 70% was reached.

The $[Ca^{2+}]_i$ variations were evaluated with the use of the calcium-specific fluorescent probe Fura 2. The preparation, enriched in parietal cells, was put in contact with 4 μM Fura2/AM, diluted in Earle's buffer, for 20 min. at 37° C. The cells were then washed and resuspended in a saline solution buffered with HEPES containing, in mM: NaCl 145, $CaCl_2$ 1, $MgCl_2$ 1, KCl 5, HEPES 10, glucose 10, pH 7.4. Each measurement was carried out on cells in suspension ($0.8 \times 10^6$/ml) at a thermostatically-controlled temperature of 37° C. and with constant magnetic stirring. The fluorescence was recorded with the use of a spectrofluorometer. The operative wavelengths were 340/380 nm for excitation and 505 nm for emission. The basal $[Ca^{2+}]_i$ values or those reached after stimulation of the cellular system were estimated according to Grynkiewicz et al [J. Biol. Chem. 260 (1985), 3440].

In the control samples, the cells were stimulated with gastrin $5 \times 10^{-8}$, whereas in the samples in which the effect of the compounds of the invention was evaluated, the cells were incubated with the compounds before the stimulation with gastrin. The results are expressed as percentage increments of $[Ca^{2+}]_i$ in comparison with the control value. The antigastrin activity of the compounds was expressed as the $IC_{50}$, that is, the concentration (in micromoles/liter) at which the response to the stimulus induced by gastrin was reduced by 50%. The results thus obtained for some compounds of the invention are given in Table 4, which also gives an index derived from the ratio between the peripheral antigastrin activity just described and the displacement activity found in the test on binding to the guinea-pig cortex receptors described above.

It can be seen from the data given in Table 4 that many of the compounds of the invention are potent inhibitors of the increase in cytosolic calcium induced by gastrin in the gastric mucous cells of the rabbit.

Essentially, the peripheral antigastrin activity accords well with the antigastrin activity obtained centrally by the binding tests shown in Table 3. In fact, in this case, compounds 19, 21, 25 and 30 were also the most potent of the compounds described, exhibiting $IC_{50\ value}$s of a nanomolar order of magnitude. Generally, the compounds of the invention show antigastrin activity in this model at concentrations 1–20 times lower than those obtained centrally and the most potent compounds are also about 50 times more active than their precursor, CR 2194 also in this model.

The antagonistic compounds tested were administered in various doses so that an $ID_{50}$, that is, the dose (in mg/kg I.V.) which could inhibit the effect of pentagastrin by 50%, could be calculated.

The results obtained, expressed as $ID_{50}$ values are given in the following table (Table 5).

TABLE 5

Inhibition ($ID_{50}$ mg/Kg I.V.) of the acid secretion induced by pentagastrin (30 mcg(kg/h) in the rat.

| Compounds | Activity (ID50) | |
|---|---|---|
| | mg/kg | micromoles/kg |
| 9 | 12.3 | 22.6 |
| 10 | 28.4 | 48.3 |
| 12 | 13.6 | 24.2 |
| 14 | 9.7 | 16.1 |
| 15 | 13.5 | 22.4 |

TABLE 4

Inhibition of the increase of cytosolic calcium induced by gastric mucous cells in the rabbit

| Compounds | IC50 micromoles /liter | Ratio IC50 Binding cortex* IC50 (gastric mucous cells) | Compounds | IC50 micromoles /liter | Ratio IC50 Binding cortex* IC50 (gastric mucous cells) |
|---|---|---|---|---|---|
| 2 | 1.50 | 0.7 | 24 | 0.03 | 4.3 |
| 6 | 0.05 | 7.6 | 25 | 0.007 | 10.0 |
| 8 | 0.06 | 3.3 | 27 | 0.23 | 0.6 |
| 9 | 0.05 | 3.0 | 28 | 0.10 | 6.5 |
| 10 | 0.20 | 3.7 | 30 | 0.008 | 12.5 |
| 11 | 0.07 | 3.1 | 34 | 0.07 | 10.4 |
| 12 | 0.06 | 1.7 | 35 | 0.12 | 14.2 |
| 14 | 0.02 | 17.0 | 38 | 0.03 | 6.0 |
| 15 | 0.03 | 7.3 | 43 | 0.07 | 14.7 |
| 16 | 0.15 | 2.0 | 47 | 0.38 | 4.5 |
| 18 | 0.20 | 1.6 | 50 | 0.03 | 15.0 |
| 19 | 0.01 | 5.0 | 51 | 0.05 | 2.4 |
| 20 | 0.03 | 7.3 | 52 | 2.33 | 1.2 |
| 21 | 0.01 | 4.0 | 53 | IN | — |
| 22 | 0.05 | 7.6 | 58 | 0.33 | 1.9 |
| 23 | 0.06 | 4.5 | CR 2194 | 0.38 | 6.3 |

*Values taken from Table 3

3) Activity Against Gastric Secretion in the Rat

The activity of the compounds of the invention against gastric secretion performed by means of a mechanism with an antigastrin effect, was examined in vivo in anaesthetized rats with the use of male animals weighing about 200 g. Gastric secretion was stimulated with pentagastrin and Lai's method [Gut 5, (1964), 327–341 ] was used, with slight modification.

After tracheotomy, the oesophagus and duodenum were cannulated. A tepid solution (37° C.) of 0.25 mM NaOH was perfused and was passed through the stomach by means of a peristaltic pump at a constant flow-rate of 1 ml/minute. After stabilization for 20 minutes, the stimulant, dissolved in a physiological solution, was perfused for 120 minutes at a dose of 30 mcg/kg/h, in a volume of 0.95 ml/hour. After perfusion for 60 minutes (the basal stimulation), the product under test was administered intravenously (I.V.) as a bolus and perfusion of the stimulant was continued for a further 60 minutes. The acid secretion was recorded continuously as a function of time.

The activity of the product was evaluated as the percentage reduction of secreted acidity after the administration of the product, in comparison with the basal acidity measured during the first 60 minutes of collection in the presence of pentagastrin alone.

TABLE 5-continued

Inhibition ($ID_{50}$ mg/Kg I.V.) of the acid secretion induced by pentagastrin (30 mcg(kg/h) in the rat.

| Compounds | Activity (ID50) | |
|---|---|---|
| | mg/kg | micromoles/kg |
| 20 | 10.9 | 17.4 |
| 21 | 7.9 | 12.6 |
| 25 | 7.1 | 11.1 |
| 30 | 15.2 | 23.7 |
| 38 | 7.0 | 10.4 |
| 50 | 12.0 | 21.4 |
| 51 | 9.0 | 15.7 |
| 58 | 10.1 | 18.3 |
| CR 2194 | 11.0 | 24.9 |

It can be seen from the data given in Table 5 that many of the compounds of the invention have a potent activity against acid secretion induced by pentagastrin in the rat in vivo.

The compounds which were most active in this experiment, such as, for example, compounds 21, 25 and 38, were found to be from 2 to 2.5 times more potent than the reference compound CR 2194 on a micromolar basis. In this case also, the stereochemistry connected with the carbon atom indicated (**) in the compounds of general formula (I) had a weak effect per se in determining the antigastrin activity but, rather, was affected by the nature of the chemical surroundings of the asymmetrical carbon atom.

In fact, for example, whereas compound 9 (R) was about twice as active as its diastereoisomer, compound 10 (S), the pair of diastereoisomers 20 and 21 had almost the same antigastrin activity and compound 14 (S) was about 1.5 times more active than its (R) diastereoisomer, compound 15.

The activity of these compounds against gastric secretion is linked specifically to their antigastrin activity. In fact, they have no anticholinergic or antihistamine (anti $H_2$) activity, being completely inactive in the experimental model described above when carbachol (30 mcg/kg/h) or histamine (2.3 mg/kg/h) was used as the stimulant.

4) Anticholecystokinin (anti CCK-A) Activity

In order to check the hypothesis that the compounds of the invention are specific CCK-B-antagonists, some of the compounds which were most active as CCK-B antagonists were tested for any CCK-A activity. The experimental model used was guinea-pig gall bladder stimulated in vitro by CCK-8, with the use of lorglumide as the reference standard.

A longitudinal strip of guinea-pig gall-bladder was put in a bath for isolated organs in the presence of Krebs buffer at a temperature of 32° C., with continuous oxygenation with an oxygen-$CO_2$ mixture (95-5 V/V).

The isometric contractions were detected by means of a force transducer and recorded. The gall bladder was contracted with the use of a CCK-8 concentration of 10 ng/ml; the antagonistic activity of the compounds towards the contracting effect of the CCK was determined with the use of various concentrations, thus determining the $IC_{50}$ value, that is, the concentration in micromoles/liter of the compound which could antagonize the contracting effect of the CCK by 50%.

The results thus obtained are shown in Table 6 which gives the compounds tested, the $IC_{50}$ values found, which were calculated by the regression method on a set of at least 3 tests for each compound tested, and an index derived from the ratio of the CCK-A- and CCK-B-antagonistic activities in vitro.

TABLE 6

Anti-CCK-A activity expressed as $IC_{50}$ in micromoles/liter on guinea-pig gall bladder in vitro.

| Compounds | CCK-A-antagonistic activity $IC_{50}$ (I) | CCK-B-antagonistic activity (*) $IC_{50}$ (II) | Ratio I/II |
|---|---|---|---|
| 9 | 5.4 | 0.05 | 108 |
| 10 | 35.8 | 0.20 | 179 |
| 15 | 4.8 | 0.03 | 160 |
| 20 | 41.9 | 0.03 | 1397 |
| 21 | 9.4 | 0.01 | 940 |
| 24 | 45.8 | 0.03 | 1527 |
| 25 | 8.5 | 0.007 | 1214 |
| 27 | 3.4 | 0.23 | 14.8 |
| 30 | 14.7 | 0.008 | 1837 |
| 50 | 4.8 | 0.003 | 160.0 |
| R-lorglumide | 0.05 | — | — |
| CR 2194 | 13.5 | 0.38 | 35.5 |

Note (*): Data taken from Table 4

It can be seen from the results given in Table 6 that the compounds of the invention are weak CCK-A antagonists, their potency being from 50 to 1000 times lower than that of R-lorglumide. By comparing these activities with the CCK-B-antagonistic activity illustrated above in Table 4, it can be concluded that the compounds of the invention are antagonists specific to the CCK-B receptor, exhibiting an affinity on average about 100 times greater for the gastrin receptor (CCK-B) than for the cholecystokinin receptor (CCK-A).

5) Anxioltic Activity

Among the possible theraupeutcal activities of the subject compounds on CNS, which are linked to imbalances of the physiological neurone levels of gastrin or other related polypeptides, is particularly interesting their potential anxiolytic activity.

It has recently been postulated that the central CCK-B receptor has an important role in anxiety. This is in accordance with studies also carried out in man, which have shown that the central CCK-B mechanisms have an important function in the mediation of panic attacks [Bradwejn, H. et al; J. Psychopharmacology 6 (1992), 345]. In order to confirm this hypothesis, the potential anxiolytic activity of some of the most potent CCK-B antagonists of the invention was evaluated with the use of the "Black and White Box test" in the mouse. This experimental model, which was carried out according to Costall et al [Pharm. Biochem. Behav. 32 (1989), 777–785], used a box with dimensions of 45×21×21(h) cm divided into 2 compartments which communicated with one another through a 13×5 cm hole. The smaller compartment (⅓ of the total area) had black walls, whereas the larger had transparent walls and was illuminated by a lamp which was placed 20 cm above the box and supplied light at 20W. Under the floor there was an activity meter which recorded the movements performed by the animal in the individual compartments. The experiment was started by placing the animal in the centre of the illuminated box; as well as movements, the time which the animal spent in the dark and in the light areas and the number of movements between the 2 compartments were then recorded for 5 minutes. A control animal generally preferred to stay in the dark compartment where it felt better protected from an unusual environmental situation which put it in a state of anxiety. In this experimental model, a compound having anxiolytic activity decreased the % of movements into the dark in comparison with the total movements, increased the movements between the two light-dark compartments, and increased the % of time spent in the light in comparison with the total time.

The results obtained are shown in Table 7, where the activities obtained with compounds 9, 21 and 51 are given, tested in comparison with diazepam. The activity of compound 9-S, the diastereoisomer of compound 9 with the S configuration of the carbon indicated * in the general formula (I), which compound has weak CCK-B-antagonistic activity in vitro (see Table 3) was also examined for comparative purposes.

TABLE 7

Anxiolytic activity in the mouse in the "Black and White Box Test"

| | DOSE mg/kg IP | N° animals | TOTAL MOVE-MENTS | MOV. DARK % TOTAL MOV. | EFF. % VS CONTROL | LIGHT-DARK MOVEMENTS | EFF. % VS CONTROL | LIGHT TIME (%) TOTAL TIME | EFF. % VS CONTROL |
|---|---|---|---|---|---|---|---|---|---|
| CONTROL* | — | 10 | 494 | 59 | — | 15.2 | — | 26.6 | — |
| COMPOUND 9 | 0.1 | 10 | 505 | 59 | 0 | 16.1 | 6 | 31.0 | 17 |
| COMPOUND 9 | 1.0 | 10 | 493 | 55 | −7 | 19.9 | 31 | 36.1 | 36 |
| COMPOUND 9 | 10.0 | 10 | 503 | 55 | −7 | 17.7 | 16 | 33.5 | 26 |
| CONTROL* | — | 10 | 523 | 60 | — | 17.2 | — | 27.8 | — |
| COMPOUND S-9 | 1.0 | 10 | 528 | 57 | −5 | 18.2 | 6 | 28.5 | 3 |
| COMPOUND S-9 | 10.0 | 10 | 495 | 62 | +3 | 14.4 | 0 | 24.9 | 0 |
| CONTROL* | — | 10 | 491 | 66 | — | 14.4 | — | 26.1 | — |
| COMPOUND 21 | 0.03 | 10 | 522 | 62 | −6 | 18.2 | 26 | 28.9 | 11 |
| COMPOUND 21 | 0.3 | 10 | 499 | 57 | −1.1 | 19.8 | 37 | 33.9 | 30 |
| COMPOUND 21 | 3.0 | 10 | 495 | 60 | −9 | 18.2 | 26 | 32.4 | 24 |
| CONTROL* | — | 10 | 473 | 69 | — | 14.8 | — | 24.0 | — |
| COMPOUND 51 | 0.1 | 10 | 472 | 61 | −12 | 17.6 | 19 | 27.0 | 12 |
| COMPOUND 51 | 1.0 | 10 | 484 | 59 | −14 | 19.8 | 34 | 35.6 | 48 |
| COMPOUND 51 | 10.0 | 10 | 436 | 62 | −10 | 20.3 | 37 | 27.8 | 16 |
| CONTROL* | — | 15 | 459 | 56 | — | 14.5 | — | 24.6 | — |
| DIAZEPAM | 1.0 | 15 | 508# | 53 | −5 | 19.9 | 37 | 29.3 | 19 |
| DIAZEPAM | 3.0 | 15 | 539# | 52 | −7 | 22.3 | 54# | 33.6 | 37 |

Note: The control group (*) received a suspension of methyl cellulose (0.5%) in a 5% solution (v/v) of dimethylsulphoxide used to dissolve the compounds under test.
(#) Significant difference in comparison with the control (P <0.01).

It can be noted from an examination of Table 7 that all the compounds of the invention tested, that is, compounds 9, 21 and 51, have anxiolytic activity without sedative activity. In fact, little or no effect on total movements was noted, with a simultaneous slight decrease in the % ratio of movements into the dark over total movements, an increase of about 20–30% in comparison with the controls in the number of light-dark movements, a similar % increase vs the controls of the % ratio of time spent in the light to total time. In general, the compounds tested had a bell-shaped curve, which is a typical profile for compounds which are active at the level of the central nervous system.

The Sinister diastereoisomer of compound 9 (that is, the compound designated S-9) was completely inactive in this model, confirming the results obtained in vitro on the binding of the guinea-pig cortex.

The conventional anxiolytic, diazepam, which was used as the active control for comparison and was tested in doses of 1 and 3 mg/kg, was active for all the parameters tested. This compound seems to be the most potent in relation to the light-dark movements parameter and its activity also seems to be qualitatively different since it also significantly increased the total movements parameter.

We claim:
1. A compound represented by Formula (I):

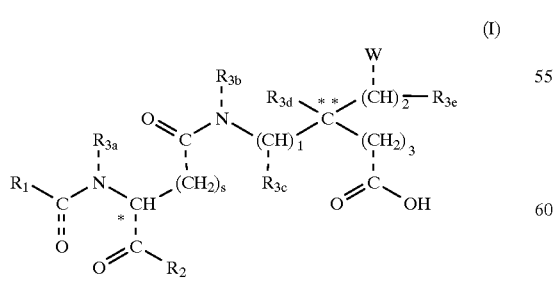

wherein s is 1 or 2,
wherein $R_1$ is a member selected from the group consisting of an unsubstituted or mono- or di-substituted phenyl group, wherein the substituents of the mono- or di-substituted phenyl group are selected from the group consisting of a chloro group, a fluoro group, a bromo group, a trifluoromethyl group, a linear or branched $C_1$–$C_4$ alkyl group, a nitro group, a cyano group, and a methoxy group; a 2-naphthyl group, a 2-(or 3-)indolyl group; and a 2-(or 3-)quinolinyl group;
wherein $R_2$ is:
$a_1$) a group represented by:

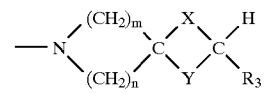

wherein m and n are each an integer of from 1 to 3, provided that the ring formed consists of at least 5 atoms, X and Y are each selected from the group consisting of (CH—$R_3$)$_z$, TCH$_2$ and CH$_2$T, where T is O or S, wherein $R_3$ is a member selected from the group consisting of H, CH$_3$ and $C_2H_5$, and wherein z is 0 or an integer of from 1 to 3, provided that the ring formed consists of at least 3 atoms,
wherein $R_{3a}$, $R_{3b}$ and $R_{3d}$ are H or CH$_3$,
wherein $R_{3c}$ and $R_{3e}$ are H or Ch$_3$,
wherein $r_1$, $r_2$ and $r_3$ are each 0 or an integer of from 1 to 2,
wherein W is a member selected from the group consisting of H, a linear or branched $C_1$–$C_6$ alkyl group, OH, OCH$_3$, SH, a benzyloxyl group, a thiomethyl group (CH$_3$—S—), or W is a member selected from the group consisting of a cycloalkane group, a heterocyclic group, a mono- or dicyclic aromatic or hydro-aromatic group having up to 10 carbon atoms, which is unsubstituted or substituted with a substituent selected from the group consisting of a fluoro group, a chloro group, a methyl group, a ethyl group, a trifluoromethyl group, a methoxy group, a cyano group, and a nitro group, or W is a CO-$R_6$ group, where $R_6$ is selected from the group consisting of:

a₂) a linear or branched amino group represented by:

wherein R₇ is selected from the group consisting of H and a linear or branched C₁–C₅ alkyl group and an alkoxyalkyl group; and R₈ is selected from the group consisting of H, a C₁–C₅ alkyl group and a (CH₂)$_z$-Ar group, wherein z has the meaning given above and Ar is an unsubstituted phenyl group or mono- or di-substituted phenyl group, wherein the substituents of the mono- or di-substituted phenyl group are selected from the group consisting of a fluoro group, a chloro group, a methyl group, an ethyl group, a trifluoromethyl group and a methoxy group; or a 1 (or 2)-naphthyl group;

b₂) a monocyclic aminoalkyl group represented by:

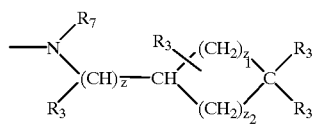

wherein z, R₃ and R₇ have the meanings given above, z₁ and z₂ are each an integer of from 1 to 4, provided that the ring formed consist of 4 to 10 carbon atoms;

c₂) a dicyclic aminospiro group represented by:

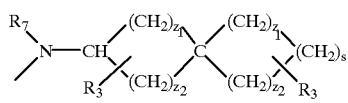

wherein R₃, R₇, s, z₁ and z₂ have the meanings given above;

d₂) a dicyclic (orthofused) amino group, represented by:

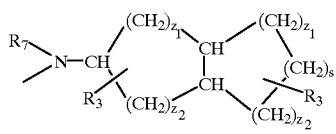

wherein R₃, R₇, s, z₁ and z₂ have the meanings given above;

e₂) a dicyclic amino group represented by:

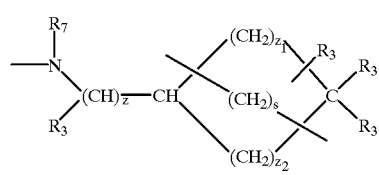

wherein R₃, R₇, s, z, z₁ and z₂ have the meanings given above;

f₂) an azacycloalkyl group represented by:

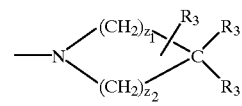

wherein R₃, z₁ and z₂ have the meanings given above;

g₂) an azadicyclic (orthofused) group, represented by:

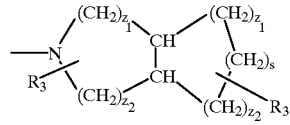

wherein R₃, s, z₁ and z₂ have the meanings given above;

h₂) a dicyclic azaspiro group represented by:

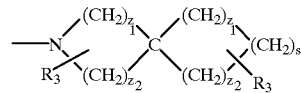

wherein R₃, s, z₁ and z₂ have the meanings given above;

i₂) an azadicyclic group represented by:

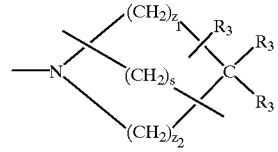

wherein R₃, s, z₁ and z₂ have the meanings given above;

l₂) an azacycloalkyl group represented by:

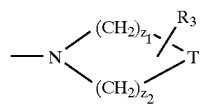

wherein R₃, z₁, z₂ and T have the meanings given above; and m₂) an aminoalkyl adamantyl group represented by:

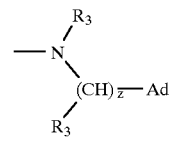

wherein R₃ and z have the meanings given above and Ad is adamantyl (1- or 2-yl);

wherein the stereochemistry of the chiral center marked by (*) in Formula (I) is in the R configuration; and the stereochemistry of the carbon atom marked by (**), which may be asymmetrical according to the substituents bonded thereto, may be R, RS or S.

2. The compound according to claim 1, wherein in Formula (I), s is 2, R₁ is a 3,5-dichlorophenyl group, R₂ is an 8-azaspiro[4.5]decan-8-yl group, $r_1$ and $r_3$ are 0, $r_2$ is 1, $R_{3a}$ is H, $R_{3b}$ is H or $CH_3$, $R_{3d}$ and $R_{3e}$ are H, W is a member selected from the group consisting of a phenyl group, a 3-indolyl group and a 1-naphthyl group, and the stereochemistry of the chiral center marked by (**) in Formula (I) is R.

3. The compound according to claim 1, wherein in Formula (I), s is 2, $R_1$ is a 3-5-dichlorophenyl group, $R_2$ is an 8-azaspiro[4.5]decan-8-yl group, $r_1$ and $r_2$ are 0, $r_3$ is 2, $R_{3a}$ is H, $R_{3b}$ is H or $CH_3$, $R_{3d}$ is H, W is a N-methylbenzylaminocarbonyl group, and the stereochemistry of the chiral center marked by (**) in Formula (I) is R, RS or S.

4. A compound according to claim 1, wherein said compound is represented by Formula (II):

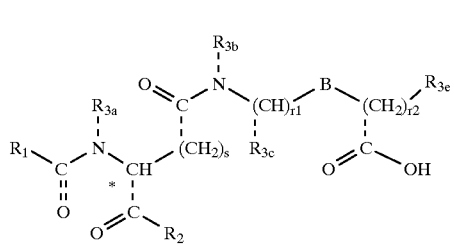

(II)

wherein $R_1$, $R_2$, $R_{3a}$, $R_{3b}$, $R_{3c}$, $R_{3e}$, s, $r_1$ and $r_2$ have the meanings given above, and B is selected from the group consisting of a cycloalkane group, a mono or dicyclic aromatic or hydro-aromatic group having up to 10 carbon atoms, an unsubstituted mono- or di-substituted phenyl group, wherein the substituents of said mono- or di-substituted phenyl group are selected from the group consisting of hydrogen, a fluoro group, a chloro group, a trifluoromethyl group, a methyl group, an ethyl group, a methoxy group, a cyano group and a nitro group.

5. The compound according to claim 4, wherein in general Formula (II), s is 2, $R_1$ is a 3-5-dichlorophenyl group, $R_2$ is an 8-azaspiro[4.5]decan-8-yl group, $r_1$ and $r_2$ are 0, $R_{3a}$ is H, $R_{3b}$ is H or $CH_3$, and B is an o-phenylene group.

6. A compound according to claim 1, wherein said compound is represented by Formula (III):

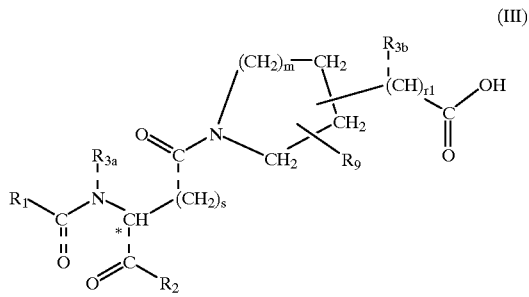

(III)

wherein $R_1$, $R_2$, $R_{3a}$, $R_{3b}$, s, m and $r_1$ have the meanings given above and $R_9$ is a member selected from the group consisting of hydrogen, a linear or branched $C_1$–$C_5$ alkyl group, a phenyl group and a benzyl group.

7. The compound according to claim 6, wherein in Formula (III) s is 2, $R_1$ is a 3,5-dichlorophenyl group, $R_2$ is a 8-azaspiro[4.5]decan-8yl group, $r_1$ is 0, $R_{3a}$ is H, m is 1 or 2 and $R_9$ is H.

8. The compound according to claim 1, wherein in Formula (I), s is 2, $R_1$ is a phenyl group substituted with a chloro group in positions 3 and 5, $R_2$ is an 8-azaspiro[4.5]decan-8-yl group, $r_1$ and $r_3$ are 0 or 1, $r_2$ is 1, W is a member selected from the group consisting of a phenyl group, a 3-indolyl group, and a 1-naphthyl group, and the stereochemistry of the chiral center marked by (**) in general Formula (I) is R.

9. A pharmaceutical composition comprising, as an active ingredient, at least one compound according to claim 1, or a pharmaceutically acceptable salt thereof, and a pharmaceutically acceptable carrier.

10. The pharmaceutical composition according to claim 9, wherein said composition is useful in the treatment of gastric ulcers.

11. The pharmaceutical composition as claimed in claim 9, wherein said composition is useful in the treatment of tumors which are sustained by gastrin or biologically active polypeptides related to gastrin.

12. The pharmaceutical composition according to claim 9, wherein said composition is useful in the treatment of non-ulcerous dyspepsia and irritable colon.

13. The pharmaceutical composition according to claim 9, wherein said composition is useful in the treatment of pathological conditions of the Central Nervous System connected with imbalances in the physiological neuron levels of gastrin or biologically active polypeptides related to gastrin.

14. The pharmaceutical composition according to claim 9, wherein said composition is useful in the treatment and prevention of eye pathological conditions induced by surgical treatment of cataracts or chronic eye inflammation.

15. The pharmaceutical composition according to claim 9, wherein said pharmaceutically acceptable carrier is selected from the group consisting of a vehicle, a binder, a flavorant, a dispersant, a preservative, a humectant and mixtures thereof.

* * * * *